United States Patent
Yun

(10) Patent No.: US 11,319,357 B2
(45) Date of Patent: *May 3, 2022

(54) METHODS, ARRANGEMENTS AND SYSTEMS FOR OBTAINING INFORMATION ASSOCIATED WITH AN ANATOMICAL SAMPLE USING OPTICAL MICROSCOPY

(71) Applicant: The General Hospital Corporation, Boston, MA (US)

(72) Inventor: Seok-Hyun Yun, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 277 days.

This patent is subject to a terminal disclaimer.

(21) Appl. No.: 16/452,247

(22) Filed: Jun. 25, 2019

(65) Prior Publication Data

US 2019/0309045 A1 Oct. 10, 2019

Related U.S. Application Data

(63) Continuation of application No. 15/690,403, filed on Aug. 30, 2017, now Pat. No. 10,351,616, which is a (Continued)

(51) Int. Cl.
*A61B 5/00* (2006.01)
*C07K 14/705* (2006.01)
(Continued)

(52) U.S. Cl.
CPC ........ *C07K 14/70503* (2013.01); *A61B 3/102* (2013.01); *A61B 3/117* (2013.01);
(Continued)

(58) Field of Classification Search
CPC .................. C07K 14/70503; A61B 5/0066
See application file for complete search history.

(56) References Cited

U.S. PATENT DOCUMENTS 3,813,613 A 5/1974 Danielmeyer et al.
4,030,827 A 6/1977 Delhaye et al.
(Continued)

FOREIGN PATENT DOCUMENTS

WO 03030726 A1 4/2003
WO 2005047813 A1 5/2005

OTHER PUBLICATIONS

Berovic et al., Observation of Brillouin Scattering from Single Muscle Fibres, European Biophysics Journal, 1989, 17 (2):69-74.
(Continued)

*Primary Examiner* — Joseph M Santos Rodriguez
(74) *Attorney, Agent, or Firm* — Quarles & Brady LLP

(57) ABSTRACT

Arrangements and methods are provided for obtaining information associated with an anatomical sample. For example, at least one first electro-magnetic radiation can be provided to the anatomical sample so as to generate at least one acoustic wave in the anatomical sample. At least one second electro-magnetic radiation can be produced based on the acoustic wave. At least one portion of at least one second electro-magnetic radiation can be provided so as to determine information associated with at least one portion of the anatomical sample. In addition, the information based on data associated with the second electro-magnetic radiation can be analyzed. The first electro-magnetic radiation may include at least one first magnitude and at least one first frequency. The second electro-magnetic radiation can include at least one second magnitude and at least one second frequency. The data may relate to a first difference between the first and second magnitudes and/or a second difference between the first and second frequencies. The second difference may be approximately between −100 GHz and 100 GHz, excluding zero.

20 Claims, 6 Drawing Sheets

Related U.S. Application Data continuation of application No. 11/672,571, filed on Feb. 8, 2007, now Pat. No. 9,777,053.

(60) Provisional application No. 60/771,916, filed on Feb. 8, 2006.

(51) Int. Cl.

| | | |
|---|---|---|
| *G01J 3/44* | (2006.01) | |
| *G01N 21/17* | (2006.01) | |
| *G01N 21/63* | (2006.01) | |
| *G01N 21/47* | (2006.01) | |
| *A61B 3/10* | (2006.01) | |
| *A61B 3/117* | (2006.01) | |
| *G01B 9/02091* | (2022.01) | |
| *G02B 21/00* | (2006.01) | |

(52) U.S. Cl.
CPC .......... *A61B 5/0059* (2013.01); *A61B 5/0066* (2013.01); *A61B 5/0073* (2013.01); *A61B 5/0084* (2013.01); *A61B 5/0095* (2013.01); *A61B 5/412* (2013.01); *A61B 5/413* (2013.01); *G01B 9/02091* (2013.01); *G01J 3/4412* (2013.01); *G01N 21/1717* (2013.01); *G01N 21/4795* (2013.01); *G01N 21/636* (2013.01); *A61B 5/0075* (2013.01); *A61B 5/0086* (2013.01); *A61B 5/0097* (2013.01); *A61B 5/4088* (2013.01); *C07K 2319/30* (2013.01); *C07K 2319/32* (2013.01); *C07K 2319/70* (2013.01); *G01N 2021/1725* (2013.01); *G01N 2021/638* (2013.01); *G01N 2201/06* (2013.01); *G01N 2201/0612* (2013.01); *G01N 2800/042* (2013.01); *G01N 2800/387* (2013.01); *G01N 2800/7023* (2013.01); *G01N 2800/7028* (2013.01); *G02B 21/0052* (2013.01)

(56) References Cited

U.S. PATENT DOCUMENTS

| | | |
|---|---|---|
| 4,479,499 A | 10/1984 | Alfano |
| 4,483,005 A | 11/1984 | Smart |
| 4,984,903 A | 1/1991 | Sweeney |
| 5,862,273 A | 1/1999 | Pelletier |
| 5,912,179 A | 6/1999 | Alvarez et al. |
| 6,002,480 A | 12/1999 | Izatt et al. |
| 6,134,003 A | 10/2000 | Tearney et al. |
| 6,422,023 B1 | 7/2002 | Dudd, Jr |
| 6,975,898 B2 | 12/2005 | Seibel |
| 7,355,716 B2 | 4/2008 | de Boer et al. |
| 7,382,949 B2 | 6/2008 | Bouma et al. |
| 7,480,058 B2 | 1/2009 | Zhao et al. |
| 7,777,891 B2 | 8/2010 | Hasegawa |
| 2009/0054763 A1 | 2/2009 | Wang et al. |
| 2014/0078512 A1 | 3/2014 | Kang et al. |

OTHER PUBLICATIONS

Lees et al., Studies of Compact Hard Tissues and Collagen by Means of Brillouin Light Scattering, Connective Tissue Research, 1990, 24(3-4):187-205.

Randall et al., Brillouin Scattering in Systems of Biological Significance, Philosophical Transactions of the Royal Society of London, Series A, Mathematical and Physical Sciences, 1979, 293(1402):341-348.

She et al., Stimulated Rayleigh-Brillouin Gain Spectroscopy, Physical Review A, 1985, 31(6):3733-3740.

Takagi et al. Application of a Microscope to Brillouin Scattering Spectroscopy, Review of Scientific Instruments, 1992, 63(12):5552-5555.

Vaughan et al., Brillouin Scattering, Density and Elastic Properties of the Lens and Cornea of the Eye, Nature, 1980, 284(5755):489-491.

METHODS, ARRANGEMENTS AND SYSTEMS FOR OBTAINING INFORMATION ASSOCIATED WITH AN ANATOMICAL SAMPLE USING OPTICAL MICROSCOPY

CROSS-REFERENCE TO RELATED APPLICATIONS

This application is a continuation of U.S. patent application Ser. No. 15/690,403, filed on Aug. 30, 2017, which is a continuation of U.S. patent application Ser. No. 11/672,571, filed on Feb. 8, 2007, which was patented as U.S. Pat. No. 9,777,053 on Oct. 3, 2017, which is based upon and claims the benefit of priority from U.S. Patent Application Ser. No. 60/771,916, filed Feb. 8, 2006, the entire disclosures of which are incorporated herein by reference.

FIELD OF THE INVENTION

The present invention relates to methods, arrangements and systems which obtain information associated with an anatomical sample using optical microscopy, and more particularly to such methods, systems and arrangements that obtain the information based on light scattering in an anatomical structure via acoustic phonons optically generated in the anatomical structure.

BACKGROUND INFORMATION

When an optical wave is propagated in a medium, a portion of its energy can be converted to the kinetic energy of the medium by exciting acoustic phonons. This process can be facilitated by various mechanisms such as thermal or electrostriction effect. The excited acoustic phonons in turn generate inelastic scattering of the optical wave, known as Brillouin scattering. The magnitude and frequency (e.g., spectrum) of the Brillouin scattered light can be determined using the acoustic phonons generated therein. Such generated photons are likely closely related to mechanical properties of the medium, such as modulus, density, and structural shape. These mechanical properties therefore can be measured by examining the Brillouin scattered light. This technique is known as Brillouin spectroscopy. Various conventional techniques to detect the Brillouin signal have been applied in physics, material science, and mechanical engineering area. In addition, the Brillouin process can be enhanced via the use of multiple optical pump waves with frequencies separated by those of the acoustic phonons in the medium.

The Brillouin microscopy generally differs from the Raman microscopy or spectroscopy in that the Brillouin microscopy involves acoustic phonons instead of vibrational phonons Raman scattering is generally based upon. Since the Brillouin shift ranges typically from 10 MHz to 10 GHz, the direct electrical detection of the acoustic wave may also be possible.

Accordingly, there is a need to overcome the deficiencies described herein above.

OBJECTS AND SUMMARY OF THE INVENTION

To address and/or overcome the above-described problems and/or deficiencies, exemplary embodiments of microscopy systems, arrangements and processes can be provided that are capable of combining the Brillouin effects with high-resolution microscopy to probe mechanical properties of an anatomical sample, such as human tissue in vivo or artificially engineered tissue. When applied to the biological tissue, these exemplary embodiments of the microscopy systems, arrangements and processes allow the biomechanical properties to be characterized at the tissue or possibly cellular level.

In one exemplary embodiment of the present invention, a pump beam can be scanned over the biological sample through an objective lens, and the beating signal between the pump and Brillouin-shifted optical waves may be detected to characterize the Brillouin spectrum. The measured spectral features of the Brillouin signal can be converted to an image, e.g., by use of a proper lookup table or computer software which associates the spectral features to data associated with images. For example, thin cross-sectional images of a thick biological sample can be obtained by using a high numerical-aperture objective lens and confocal detection.

According to another exemplary embodiment of the present invention, a secondary pump beam with a different optical frequency can be used to facilitate a generation of acoustic phonons through stimulated or forced Brillouin scattering. In an exemplary variant of the present invention, anti-stokes Brillouin scattering technique(s) can be implemented using multiple pump beams. Various pump and probe techniques, and/or heterodyne or spectrometer-based detection techniques can be used.

Tissue biomechanical properties can be altered in a variety of disease states, and therefore may be appropriate targets for non-invasive diagnosis. A further exemplary embodiment of the systems, arrangements and processes of the present invention can make it possible to obtain the information about intrinsic tissue biomechanical properties that are not readily available by other ways, and therefore determine a wide range of applications in biology and medicine. For example, the Brillouin microscopy can become a clinical tool for the detection of early-stage cancers or intra-operative determination of tumor margins. Considering that tumors are generally stiffer than surrounding healthy tissue, the Brillouin spectrum of a tumor can possibly exhibit a stronger magnitude at high frequencies than that of normal tissues. Atherosclerosis is another medical area the Brillouin microscopy may be useful for characterizing stress and tissue compliance to identify plaques at risk for causing an acute coronary event. For example, a scanning catheter or handheld endoscope may be used to perform the Brillouin measurement in living patients.

Thus, in accordance with one exemplary embodiment of the present invention, arrangements and methods are provided for obtaining information associated with an anatomical sample. For example, at least one first electro-magnetic radiation can be provided to the anatomical sample so as to generate at least one acoustic wave in the anatomical sample. At least one second electro-magnetic radiation can be produced based on the acoustic wave. At least one portion of at least one second electro-magnetic radiation can be provided so as to determine information associated with at least one portion of the anatomical sample.

According to another exemplary embodiment of the present invention, the information based on data associated with the second electro-magnetic radiation can be analyzed. The first electro-magnetic radiation may include at least one first magnitude and at least one first frequency. The second electro-magnetic radiation can include at least one second magnitude and at least one second frequency. The data may relate to a first difference between the first and second magnitudes and/or a second difference between the first and second frequencies. The second difference may be approximately between −100 GHz and 100 GHz, excluding zero.

In another exemplary embodiment of the present invention, at least one fourth arrangement configured to image the portion of the anatomical sample based on data associated with the second electro-magnetic radiation can be provided. Further, at least one fifth arrangement configured may be provided to translate the at least one electro-magnetic radiation across the anatomical sample. The fifth arrangement may include at least one lens, and the lens can focus the first electro-magnetic radiation and can collect the second electro-magnetic radiation. The second arrangement can include a spectral filter which may facilitate a determination of a spectrum of the second electro-magnetic radiation. The information can be associated with a biomechanical property of the anatomical sample. The anatomical sample may be a living subject.

According to still another exemplary embodiment of the present invention, the first electro-magnetic radiation may have a center wavelength which is approximately between 0.5-1.8 μm. The first electro-magnetic radiation can have a line width which is smaller than approximately 100 MHz. The first electro-magnetic radiation can have a form of a plurality of pulses, and the duration of each of the pulses may be longer than approximately 10 ns. The first electro-magnetic radiation can also include at least two first electro-magnetic radiations, a first one of the first electro-magnetic radiations possibly having a first frequency, and a second one of the first electro-magnetic radiations possibly having a second frequency. A difference between the first and second frequencies may be between approximately zero and 100 GHz. It is possible to receive at least one third electro-magnetic radiation which has at least one third magnitude and at least one third frequency. The second frequency may be determined as a function of the first and third frequencies. The third electro-magnetic radiation can be forwarded from an electro-magnetic radiation source.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which.

Figure 1A:
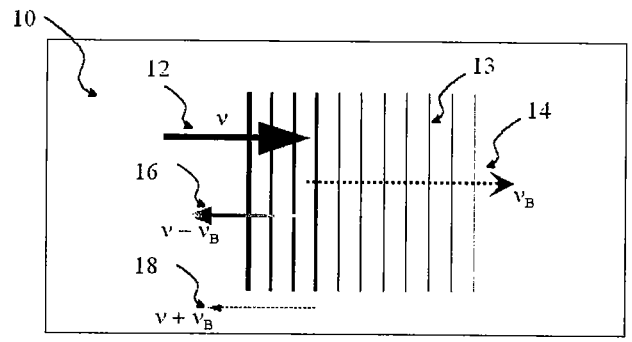
FIG. 1A is a first illustration of an exemplary embodiment of an application and a Brillouin effect of a method according to the present invention.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

Figure 1B:
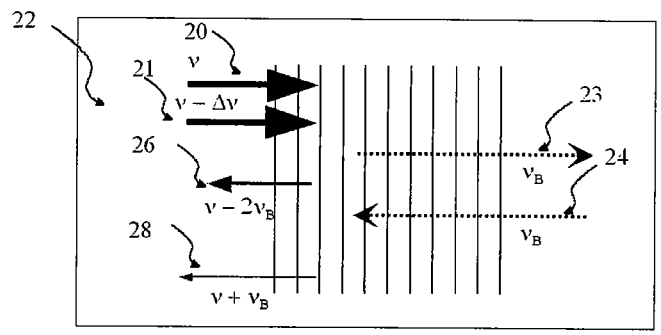
FIG. 1B is a second illustration of an exemplary embodiment of the application and a Brillouin effect of the method according to the present invention.

FIGS. 1A and 1B illustrate exemplary application of an exemplary embodiment of a method which implement a principle of Brillouin scattering according to the present invention. For example, a monochromatic pump light with a frequency $\nu=\omega/2\pi$ can be provided incident on a medium under test. An exemplary generation of an acoustic wave can be initiated by seed photons which may quantum-mechanically originate from a vacuum fluctuation. There may be one seed photon per unit frequency bandwidth.

The pump and seed photons may interfere with one another, and generate a mechanical stress modulation in the medium via thermal or electrostriction effects. When the stress modulation is phase-matched to one of the characteristic acoustic phonon modes in the medium, the corresponding acoustic phonons can develop efficiently through a coherent process. The excited acoustic phonons in turn may create a refractive-index modulation in the medium, and generate inelastic scattering of photons. The energy and momentum of the photons can be modified by an inelastic scattering procedure. The magnitude of a frequency shift in the scattered photons can be substantially or approximately equal to that of the acoustic phonons. This exemplary procedure is called "Brillouin phenomenon" or "Brillouin scattering." Although both Stokes and anti-Stokes components can be generated, typically Stokes Brillouin component (e.g., frequency down shifted) would likely be predominantly generated.

Exemplary phase matching conditions between the pump scattering light and the acoustic wave can be expressed as:

$$\omega_A = \omega_p - \omega_s \quad (1)$$

$$\vec{k}_A = \vec{k}_p - \vec{k}_s \quad (2)$$

where $\omega$ and $k$ are angular frequency and wave number, respectively, and the subscript A, p, and s represent acoustic phonons, pump and scattering (or signal) photons, respectively. The frequency of the phase matched phonons, e.g., the difference between the pump and scattering photons, can be given by $$\omega_A = |\vec{k}_A| V_A = 2 V_A |\vec{k}_p| \sin(\theta/2) \quad (3)$$

Where $V_A$ denotes the speed of the acoustic phonon mode (e.g., an acoustic wave) in the medium and $\theta$ is an angle between the pump and scattering photons (e.g., optical waves). The Brillouin shift, as expressed in Eq. (3), can increase with the acoustic speed. In a solid state medium, the acoustic speed is proportional to the square root of the modulus. When the two waves propagate at the opposite direction, $\theta=180°$, the magnitude of Brillouin shift can become maximum.

For example, FIG. 1A illustrates a backward Brillouin scattering effect in an exemplary implementation of an exemplary embodiment of the present invention. The pump wave 12 with frequency $\nu$ is incident on a medium 10, and generates an acoustic wave represented by the wave fronts 13 and its wave vector 14 corresponding to an acoustic frequency $\nu_B$. The Brillouin scattered light 16 satisfying the phase matching condition may have a frequency $\nu-\nu_B$. For example, if there are a large number of acoustic modes present in a sample; then the spectrum of the Brillouin scattered light may consist of multiple lines characterized by their frequencies, magnitudes, and spectral widths, all of which may be related to the mechanical properties of the sample. If the medium 10 is optically transparent, no Antistokes Brillouin light 18 with a frequency higher than that of the pump wave would likely be produced. In a turbid medium such as biological tissue, the light can experience a strong elastic Mie or Rayleigh scattering, in addition to much weaker inelastic Brillouin or Raman scattering. The elastically scattered light, diffused in random directions, may interfere with each other, and can result in a detectable Anti-stokes Brillouin light.

When the acoustic wave is initially provided, the Brillouin phenomenon can be accelerated because of the presence of the scattered light. The scattered light, coherent with the pump light, may amplify the resonant acoustic wave, which in turn may enhance the Brillouin scattering. This positive feedback can result in a strong Brillouin shifted scattered light, e.g., a procedure called "stimulated Brillouin scattering." In a long optical fiber, this exemplary procedure can arise at a very low pump power of several tens of mW, and may be characterized by the Brillouin gain provided by $$g_B(\nu_B) = \frac{2\pi n^2 p_{12}^2}{c \lambda_p^2 \rho_0 V_A \Delta \nu_B} \omega_p - \omega_s \quad (4)$$

where n is the refractive index, $p_{12}$ is the elasto-optic coefficient, and $\rho$ is the density.

FIG. 1B shows another application of a Brillouin interaction according to the exemplary embodiment of the present invention in a turbid medium 22 initiated by two pump waves 20, 21 with a frequency difference of $\Delta\nu$. The exemplary elastic scattering of the pump waves can stimulate the excitation of acoustic waves (phonons) propagating multiple directions. In the exemplary illustration of FIG. 1B, only two waves propagating along the forward and backward directions 23, 24. The resulting Brillouin scattered light has multiple spectral lines including the Stokes 26 and anti-Stokes 28 components. This exemplary application according to the present invention may be used to enhance the generation of the anti-Stokes line. For example, the maximum Brillouin efficiency can be achieved when the frequency difference substantially matches the frequency of at least one of the acoustic waves (phonons) generated in this manner.

Figure 2:
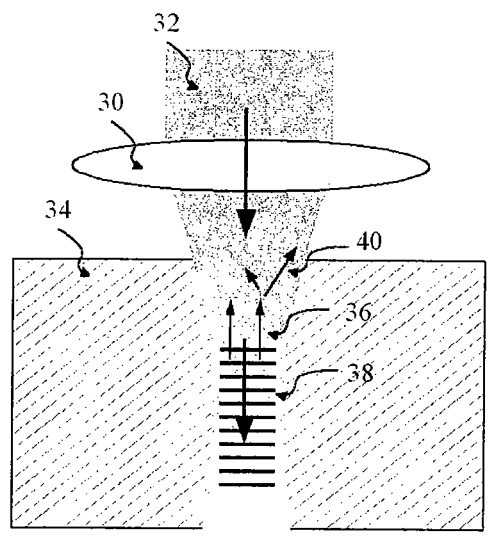
FIG. 2 is an illustration of a Brillouin scattering procedure in tissue using the exemplary embodiment of the method according to the present invention.

Because the efficiency of Brillouin scattering is likely proportional to an optical intensity, a higher efficiency can be obtained by focusing the pump light to the sample. By focusing, higher spatial discrimination or resolution can be obtained. FIG. 2 illustrates an exemplary use of objective lens 30 in accordance with an exemplary embodiment of the present invention for both focusing a pump beam 32 to a sample 34, and collecting a backward propagating Brillouin scattered light 36. Such exemplary detection scheme can be called the "epi configuration." For example, FIG. 2 shows an associated acoustic wave 38 propagating forward, as well as elastically scattered, diffused waves 40. A portion of the elastically scattered light within the numerical aperture of the lens may be also collected. Because the Brillouin process can produce a phase conjugation, the backward Brillouin scattering may be efficiently collected, even with a low numerical-aperture objective lens.

Brillouin spectroscopy is a technique that can measure the spectrum of the Brillouin scattered light, thereby allowing the properties of inherent acoustic phonons of a medium. The Brillouin spectrum may be closely related to the mechanical properties of the medium through the phase matching conditions represented in Equations (1) and (2) (e.g., in their simplest forms).

Figure 3A:
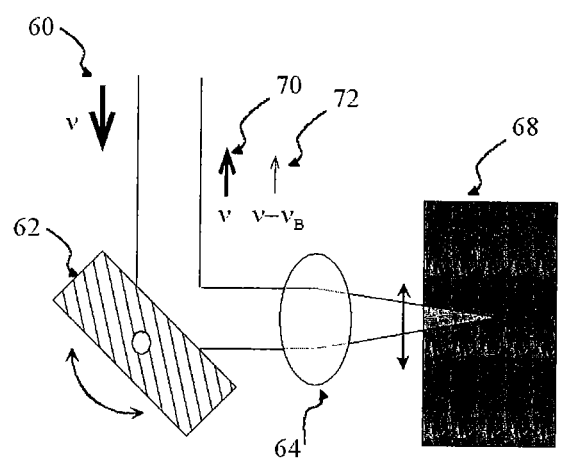
FIG. 3A is a first illustration of a further application of the exemplary embodiment of the method according to the present invention which produces a beam scanning Brillouin imaging.
Figure 3B:
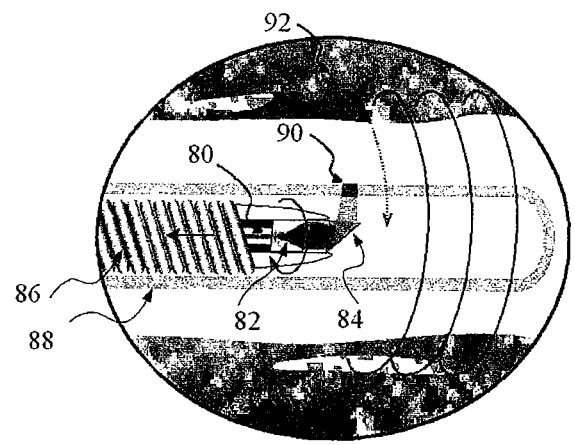
FIG. 3B is a second enlarged illustration of the application of the exemplary embodiment of the method shown in FIG. 3A.

One of the important features of an exemplary embodiment of the present invention is an image generation feature. Using a predetermined or calculated conversion table, the spatial variation of the Brillouin spectra may be presented as an image. To generate images, the pump or probe beam can be scanned laterally across the sample, and/or the sample can itself be translated. FIGS. 3A and 3B illustrate two respective beam scanning applications in accordance with an exemplary embodiment of the present invention which can use a galvanometer and rotational catheter. As shown in FIG. 3A, the pump wave 60 may be reflected by a galvanometer-mounted mirror 62, and focused by an objective lens 64 to a medium 68. Light collected by the objective lens 64 in the epi mode can consist of a backscattered component 70 and a Brillouin shifted component 72. Other conventional scanners can be used, including but not limited to polygonal mirror scanners and MEMS mirrors. FIG. 3B depicts an exemplary beam-scanning application that uses an exemplary embodiment of an arrangement according to the present invention based on a fiber-optic catheter or endoscope for an application to, for example, luminal organ imaging. For example, a catheter can include a single mode fiber 80, a focusing lens 82, a prism 84, a drive shaft 86, and a protective sheath 88. A catheter core, rotated inside the stationary sheath 88, can scan across the tissue 92 using an optical beam 90 in a helical manner.

Figure 4A:
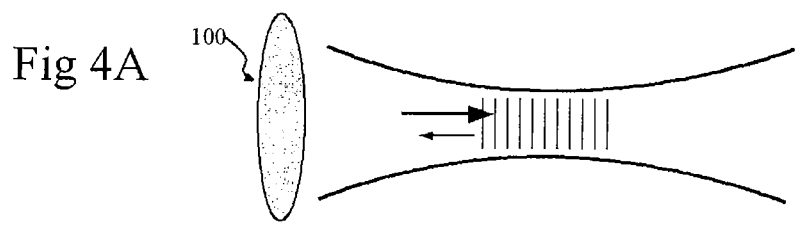
FIG. 4A is a first illustration of a beam focusing procedure implemented by the exemplary embodiment of the method according to the present invention in an exemplary embodiment of an arrangement according to the present invention.
Figure 4B:
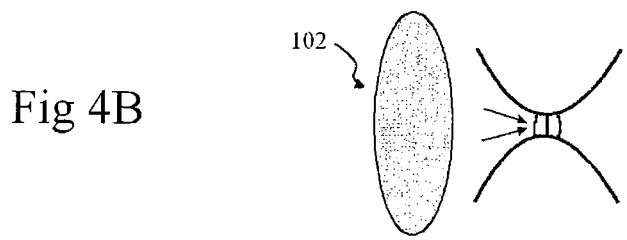
FIG. 4B is a second illustration of a beam focusing procedure implemented by the exemplary embodiment of the method as shown in FIG. 4A
Figure 4C:
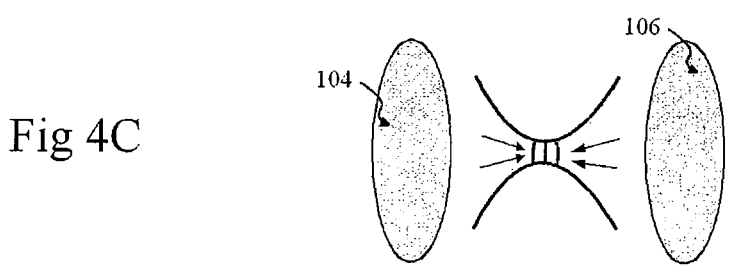
FIG. 4C is a third illustration of a beam focusing procedure implemented by the exemplary embodiment of the method as shown in FIGS. 4A and 4B.

The beam size of the pump beam at the sample can determine the spatial resolution. When a coarse spatial resolution is sufficient, it is possible to use a collimated beam. As shown in FIG. 4A, an exemplary implementation of an objective lens 100 with a low numerical aperture ("NA") can result in a low transverse resolution. With the longitudinal interaction length likely being long and well defined (FIG. 4A); an objective lens 102 with a high NA may provide better transverse and axial resolution, as shown in FIG. 4B. With the high NA, the Brillouin interaction length is likely to be short, and the phase matching can be met over a large solid angle. In both cases, the backward-propagating Brillouin light may be detected in the epi configuration. FIG. 4C depicts another exemplary implementation an use of the exemplary embodiments of the method and arrangement according to the present invention using at leas two objective lenses 104, 106. This scheme, however, may not be appropriate for thick tissue or in vivo applications.

Figure 5:
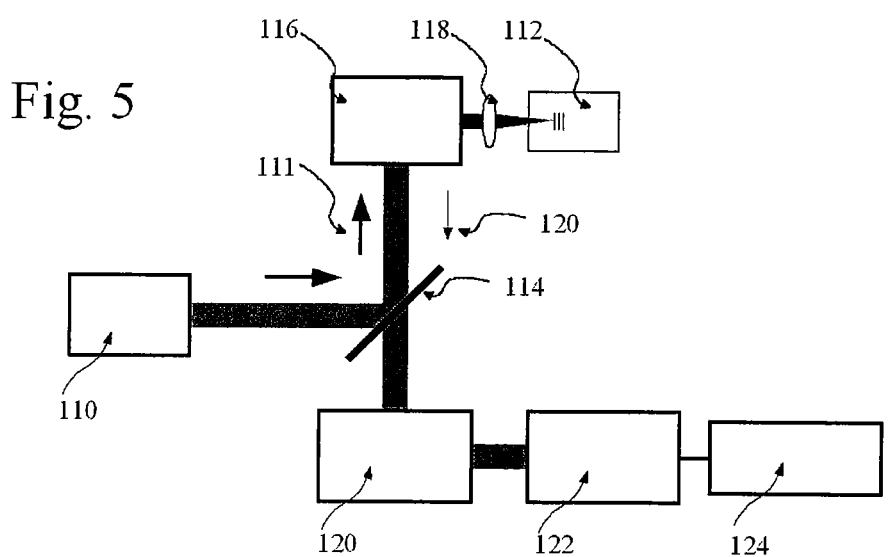
FIG. 5 is a block diagram of an exemplary embodiment of a scanning-beam Brillouin spectroscopy arrangement in accordance with the present invention.

FIG. 5 depicts a block diagram pf an exemplary embodiment of an arrangement according to the present invention. For example, the arrangement of FIG. 5 includes a light source 110, preferably a monochromatic laser emitting visible or infrared light source, and a pump beam/wave 111 that can be illuminated to a sample 112 through a beam splitter 114, a beam scanner 116, and an objective lens 118. The light source 110 can be, but not limited to, a cw single frequency laser with a center wavelength between 0.5 and 1.8 microns and a narrow line width, typically less than 100 MHz, providing temporal coherence longer than the lifetime of phonons. Another preferred type of light source is a Q-switched single frequency laser. The pulse repetition rate may range from 1 to 100 kHz, and the pulse duration from 10 ns to 1 μs. The Q-switched pump light can result in higher Brillouin generation efficiency because the intensity is higher than that of cw light at the same average power level. The light source 110 may utilize or include an optical arrangement to deliver more than one frequency components (illustrated in FIGS. 8A and 8B). The lateral step size of the beam scan can be approximately equal to the focal spot size of the pump beam/wave 111 in the sample 112.

The scattered light 120 provided from the sample 112 and collected by the objective lens 118 may originate from both elastic and inelastic scattering. The spectrum of the scattered light may be measured using a spectrally-selective arrangement 120, such as scanning filters, etalons, virtual interferometer phase arrays, or spectrometers. Various scanning filters are known in the art, including but not limited to a Fabry-Perot interferometer. For example, the Brillouin shift can be as high as several tens of GHz. The exemplary Fabry-Perot scanning interferometer may have a free spectral range of 50 GHz, and finesse of 1000. The spectrally selected optical photons may then be converted to electrical signals at a detector 122 (e.g., a photo-multiplier tube, avalanche photodiode, or charge-coupled-device array).

Figure 6A:
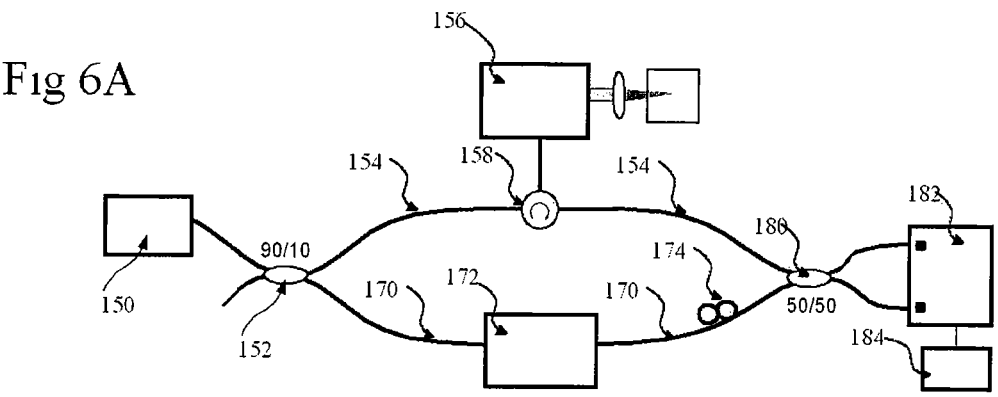
FIG. 6A is a block diagram of a first exemplary embodiment of a Brillouin microscopy arrangement that can use interferometry in accordance with the present invention.
Figure 6B:
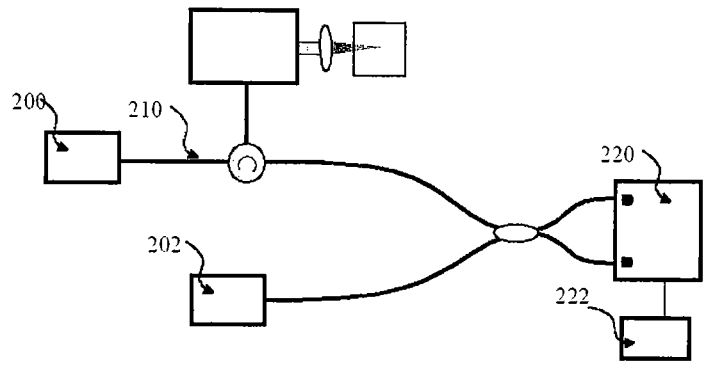
FIG. 6B is a block diagram of a second exemplary embodiment of the Brillouin microscopy arrangement that can use interferometry in accordance with the present invention.

Other exemplary embodiments of the present invention that use fiber-optic heterodyne interferometers are shown in the block diagrams of FIGS. 6A and 6B. In FIG. 6A, a single-frequency laser 150 is shown to be coupled to a fiber-optic beam splitter 152 with an exemplary splitting ratio of approximately 90:10. One optical path, termed a sample arm 154, can be connected to a beam scanner 156 via a circulator 158, and the other path, termed a reference arm 170, may contain a frequency shifter 172 such as an acousto-optic or electro-optic modulator. Both the sample and reference arms 154, 170 may be combined at another fiber-optic beam splitter 180, with, e.g., equal splitting ratios. The interference signal between the backscattered light in the sample arm 154 and the frequency-shifted reference light in the reference arm 170 can be measured by a dual balanced receiver 182, and processed using a computer 184. The frequency shifter 172 can be used to decrease the beat frequency between scattered and reference light, and a polarization controller 174 may also be utilized, as shown in FIG. 6A. According to another exemplary embodiment of the present invention, an electrical spectrum analyzer may replace or complement the computer 184. Alternatively, the Brillouin spectra may be determined by tuning the magnitude of frequency shift by the shifter 172 and measuring the beat signal with a low-bandwidth detector 182.

FIG. 6B depicts a block diagram of another exemplary configuration according to a further exemplary embodiment of the present invention that uses two monochromatic lasers 200, 202, with a tunable frequency difference. One laser 200 is coupled to a sample arm 210 for delivering the pump wave. The second laser 202 can serve as a local oscillator to provide the reference light with a frequency detuned from that of the pump source by a predetermined amount. The frequency of the local oscillator can be close to that of one of Brillouin signal light, and the beat frequency may be measured by a detector 220. For example, the line widths of the pump source 200 and the local oscillator 202 should be significantly narrow, and typically less than 100 kHz, to effect a temporal coherency between the scattered and reference light.

Figure 6C:
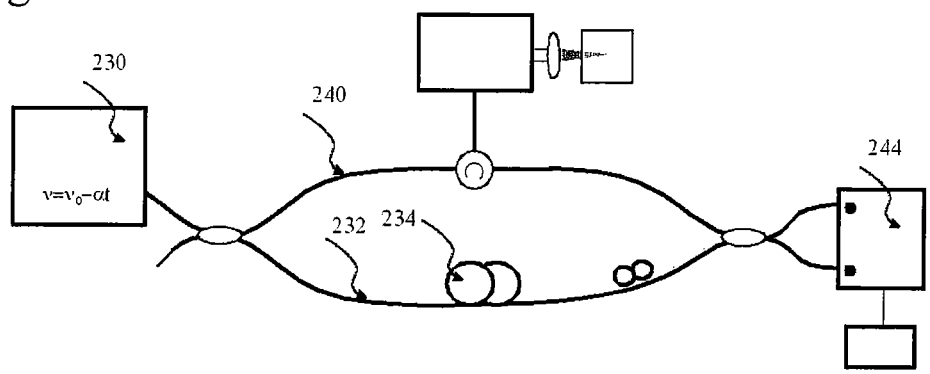
FIG. 6C is a block diagram of a third exemplary embodiment of the Brillouin microscopy arrangement that can use interferometry in accordance with the present invention.

FIG. 6C illustrates a block diagram of yet another exemplary embodiment of the arrangement according to the present invention based on a frequency-swept laser 230 that can be preferably either one of a mode-hop-free extended-cavity semiconductor laser, temperature-tuned distributed feedback laser, and cavity-modulated solid-state laser. The reference arm 232 may contain a delay line 234 providing an optical delay by a fixed amount and/or a variable amount controlled by the length difference between the reference and sample arms 232, 240. The length mismatch between the two arms can be selected as follows:

$$\Delta L \approx \frac{c}{n\alpha} v_B, \qquad (5)$$

where c is the speed of light, n is the refractive index of medium, α is the tuning speed, and $v_B$ is the frequency of acoustic phonons of interest. Pursuant to such selection, the electrical beat frequency measured by a detector 244 can be significantly smaller than the acoustic frequency. On the other hand, when the path lengths of the two arms 232, 240 are substantially matched, such exemplary measurement technique may be similar to the optical frequency domain reflectometry. The interference signal measured as a function of wavelength can be processed via a Fourier transform to produce an axial profile of elastic backscattering coefficients. Similarly, with appropriate length mismatch, similar signal processing may yield an axial profile of Brillouin scattering coefficients.

Figure 7A:
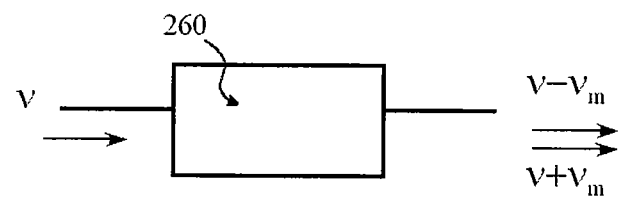
FIG. 7A is an illustration of a first stage in generating an exemplary two-frequency pump wave using an exemplary embodiment of a method and arrangement in accordance with the present invention.
Figure 7B:
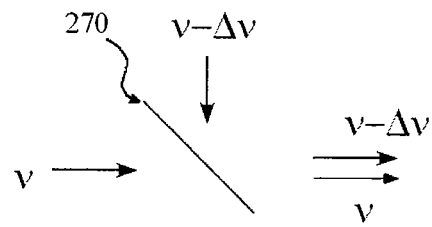
FIG. 7B is an illustration of a second stage in generating the exemplary two-frequency pump wave in conjunction with the generation shown in FIG. 7A.
Figure 7C:
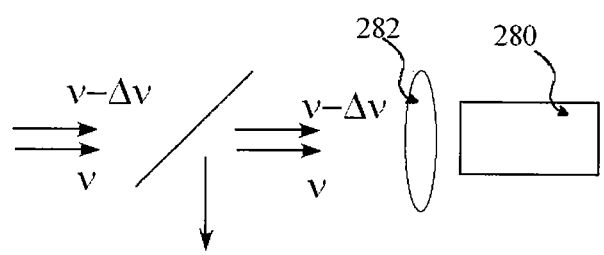
FIG. 7C is an illustration of a third stage in generating the exemplary two-frequency pump wave in conjunction with the generation shown in FIGS. 7A and 7B.
Figure 7D:
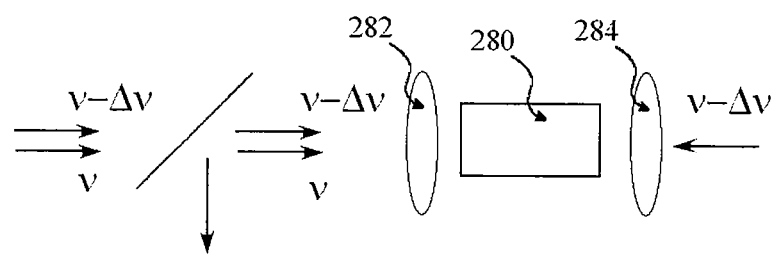
FIG. 7D an illustration of is a fourth stage in generating the exemplary two-frequency pump wave in conjunction with the generation shown in FIGS. 7A-7C.

FIGS. 7A-7D depict various stages of two different exemplary source arrangements according to an exemplary embodiment of the present invention which are capable of producing the pump wave consisting of two different frequency components. The Brillouin spectroscopy based on such two-frequency pump wave is illustrated in FIG. 1B and described herein above. For example, in FIG. 7A, an electro-optic modulator with a proper DC bias can produce two sidebands from a monochromatic laser input. In FIG. 7B, two low-drift monochromatic lasers may be combined with a beam combiner 270. In the epi configuration, the combined pump waves may be delivered to a sample 280 through an objective lens 282, as shown in FIG. 7C. In a transmission configuration, a secondary objective lens 284 may be used to launch one of the two frequency components in the opposite direction, as shown in FIG. 7D.

Figure 8A:
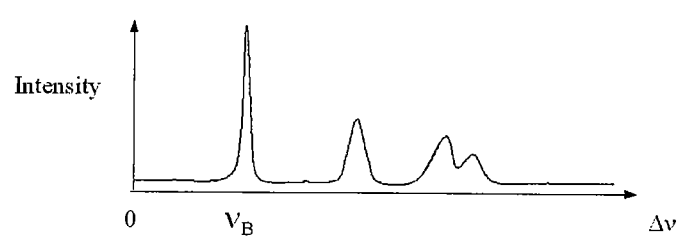
FIG. 8A is a first exemplary illustration of a Brillouin signal generation using the exemplary embodiment of the method and arrangement in accordance with the present invention.
Figure 8B:
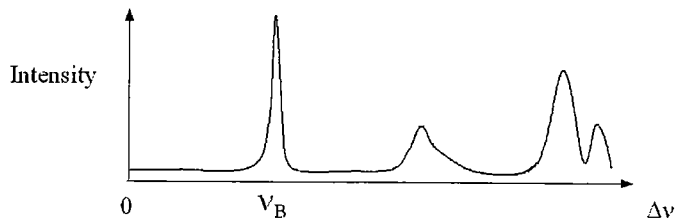
FIG. 8B is a second exemplary illustration of the Brillouin signal generation using the exemplary embodiment of the method and arrangement in accordance with the present invention.
Figure 8C:
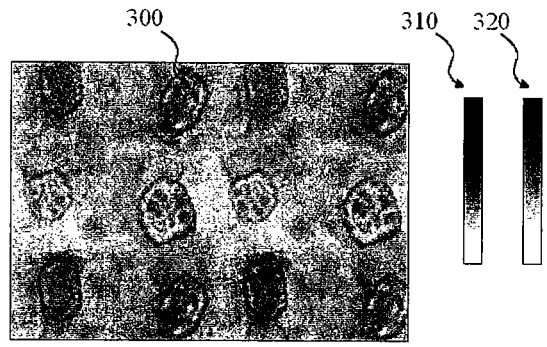
FIG. 8C is a illustration of an image produced by the signals shown in FIGS. 8A and 8B using the exemplary embodiment of the method and arrangement in accordance with the present invention.

FIGS. 8A and 8B illustrate exemplary Brillouin spectra obtained from two different locations in a sample according to the exemplary embodiment of the present invention. For example, the difference between the two spectra, represented in these figures by the magnitude of $v_g$, may indicate a difference in stiffness between the two locations. An image 300 (shown in FIG. 8C) can be formed based on the measured Brillouin signal and by using a grayscale look up table 310 and/or a false color lookup table 320. The lookup table(s) 310, 320 may be based on the magnitude and/or the frequency of one or more specific Brillouin peaks.

Figure 9A:
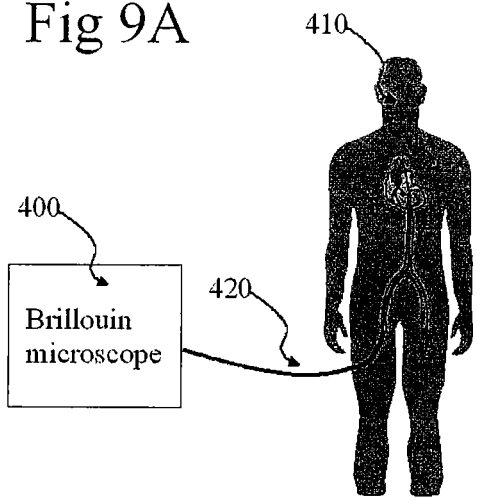
FIG. 9A is an illustration of a medical application using an exemplary embodiment of a catheter in accordance with the present invention.
Figure 9B:
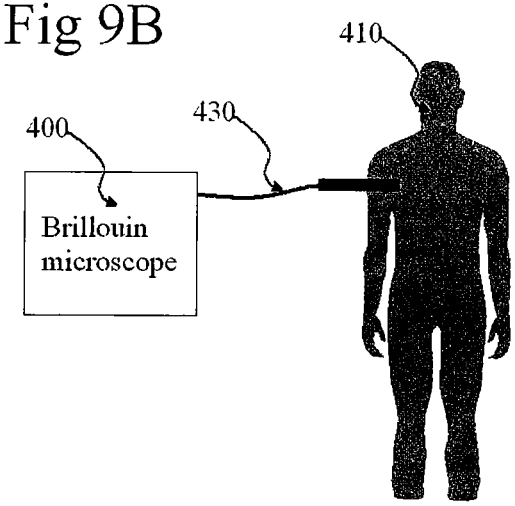
FIG. 9B is an illustration of a medical application using an exemplary embodiment of an endoscope in accordance with the present invention.

FIGS. 9A and 9B illustrates possible exemplary clinical applications of Brillouin microscopy 400 in human 410 by use of a fiber-optic catheter 420 or endoscope 430 in accordance with an exemplary embodiment of the present invention. The catheter 420 may have a similar configuration as shown in FIG. 3B. and described above The endoscope 430 may employ a two-axis XY beam scanning actuator, such as MEMS scanners. Potential applications of Brillouin microscopy can include tissue characterization based on biomechanical properties, cancer diagnosis, tumor margin determination, wound healing monitoring, tissue ablation monitoring, and tissue engineering among many.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system, spectral domain OCT (SD-OCT) system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

The invention claimed is:

1. An arrangement comprising:
   at least one first arrangement configured to provide at least one first electro-magnetic radiation to a sample so as to interact with at least one acoustic wave in the sample, wherein at least one second electro-magnetic radiation is produced based on the at least one acoustic wave and the at least one acoustic wave is amplified as a result of an interaction with the second electro-magnetic radiation;
   at least one second arrangement configured to receive at least one portion of the at least one second electro-magnetic radiation; and
   at least one third arrangement configured to determine information associated with a mechanical property of at least one portion of the sample based on a measurement of at least one of a magnitude or frequency of a spectral peak in a spectrum of the at least one second electro-magnetic radiation.

2. The arrangement of claim 1, wherein the at least one first electromagnetic radiation has a form of a plurality of pulses.

3. The arrangement of claim 1, further comprising at least one fourth arrangement configured to image the at least one portion of the sample based on data associated with the at least one second electro-magnetic radiation.

4. The arrangement of claim 3, wherein the at least one first electro-magnetic radiation includes at least one first magnitude and at least one first frequency, wherein the at least one second electro-magnetic radiation includes at least one second magnitude and at least one second frequency, and wherein the data relates to at least one of a first difference between the first and second magnitudes or a second difference between the first and second frequencies.

5. The arrangement of claim 4, wherein the second difference is between −100 GHz and 100 GHz, excluding zero.

6. The arrangement of claim 1, wherein the at least one second arrangement includes a spectral filter which facilitates a determination of the spectrum of the at least one second electro-magnetic radiation.

7. The arrangement of claim 1, wherein the information is associated with a mechanical property of the sample.

8. The arrangement of claim 1, wherein the sample is a living subject.

9. The arrangement of claim 1, wherein the sample is at least one of an organ, a tissue, or a cell.

10. The arrangement of claim 1, wherein the at least one first electromagnetic radiation has a center wavelength which is between 0.5-1.8 µm.

11. A method for obtaining information associated with a sample, comprising:
   providing at least one first electro-magnetic radiation to the sample so as to interact with at least one acoustic wave in the sample, wherein at least one second electro-magnetic radiation is produced based on the at least one acoustic wave and the at least one acoustic wave is amplified as a result of an interaction with the second electro-magnetic radiation;

receiving at least one portion of at least one second electro-magnetic radiation; and determining information associated with a mechanical property of at least one portion of the sample based on a measurement of at least one of a magnitude or frequency of a spectral peak in a spectrum of the at least one second electro-magnetic radiation.

12. The method of claim 11, wherein the at least one first electromagnetic radiation has a form of a plurality of pulses.

13. The method of claim 11, further comprising imaging the at least one portion of the sample based on data associated with the at least one second electro-magnetic radiation.

14. The method of claim 13, wherein the at least one first electro-magnetic radiation includes at least one first magnitude and at least one first frequency, wherein the at least one second electro-magnetic radiation includes at least one second magnitude and at least one second frequency, and wherein the data relates to at least one of a first difference between the first and second magnitudes or a second difference between the first and second frequencies.

15. The method of claim 14, wherein the second difference is between −100 GHz and 100 GHz, excluding zero.

16. The method of claim 11, wherein receiving at least one portion of at least one second electro-magnetic radiation includes determining the spectrum of the at least one second electro-magnetic radiation using a spectral filter.

17. The method of claim 11, wherein the information is associated with a mechanical property of the sample.

18. The method of claim 11, wherein the sample is a living subject.

19. The method of claim 11, wherein the sample is at least one of an organ, a tissue, or a cell.

20. The method of claim 11, wherein the at least one first electromagnetic radiation has a center wavelength which is between 0.5-1.8 μm.

* * * * *